(12) United States Patent
Dreier et al.

(10) Patent No.: US 9,988,344 B2
(45) Date of Patent: Jun. 5, 2018

(54) ZINC CLUSTER COMPOUNDS AND THEIR USE AS CATALYSTS IN THE REACTION OF AMINES WITH DIALKYL CARBONATES

(71) Applicant: Covestro Deutschland AG, Leverkusen (DE)

(72) Inventors: Thorsten Dreier, Dusseldorf (DE); Stefan Wershofen, Monchengladbach (DE); Anton Vidal, Tarragona (ES); Robert Haak, Tarragona (ES)

(73) Assignee: Covestro Deutschland AG, Leverkusen (DE)

( * ) Notice: Subject to any disclaimer, the term of this patent is extended or adjusted under 35 U.S.C. 154(b) by 0 days. days.

(21) Appl. No.: 14/890,053

(22) PCT Filed: May 19, 2014

(86) PCT No.: PCT/EP2014/060174
§ 371 (c)(1),
(2) Date: Nov. 9, 2015

(87) PCT Pub. No.: WO2014/187756
PCT Pub. Date: Nov. 27, 2014

(65) Prior Publication Data
US 2016/0194277 A1    Jul. 7, 2016

(30) Foreign Application Priority Data
May 22, 2013  (EP) ..................................... 13168788

(51) Int. Cl.
| | | |
|---|---|---|
| *C07F 3/00* | (2006.01) | |
| *C07C 269/04* | (2006.01) | |
| *B01J 31/22* | (2006.01) | |
| *C07C 51/41* | (2006.01) | |
| *C07C 65/21* | (2006.01) | |

(52) U.S. Cl.
CPC ......... *C07C 269/04* (2013.01); *B01J 31/2208* (2013.01); *C07C 51/418* (2013.01); *C07C 65/21* (2013.01); *B01J 2231/34* (2013.01); *B01J 2531/26* (2013.01)

(58) Field of Classification Search
CPC ..... C07C 269/04; C07C 51/418; C07C 65/21; B01J 31/2208; C07F 3/06
USPC ........................................ 556/131, 132, 135
See application file for complete search history.

(56) References Cited

U.S. PATENT DOCUMENTS

| | | | |
|---|---|---|---|
| 4,268,683 | A | 5/1981 | Gurgiolo |
| 5,347,034 | A | 9/1994 | Hammen et al. |
| 6,992,214 | B2 | 1/2006 | Cesti et al. |
| 8,513,453 | B2 | 8/2013 | Wershofen et al. |
| 2003/0171526 | A1 | 3/2003 | Cesti et al. |

FOREIGN PATENT DOCUMENTS

| | | |
|---|---|---|
| CA | 2072034 | 6/1992 |
| EP | 0065026 | 5/1981 |
| EP | 1958940 | 12/2006 |

OTHER PUBLICATIONS

Wojciech et al, Inorganic Chemistry, (2012), 51(13), pp. 7410-7412.*
Bury et al., Inorganic Chemistry, vol. 51, No. 13, pp. 7410-7412 (2012).*
Baba et al., "Catalytic Synthesis of Dimethyl toluene-2,4-dicarbamate by the Methoxycarbonylation of 2,4-Toluenediamine with Dimethyl Carbonate Using Zn(OAc)2 H2O," Science and Technology in Catalysis, 2002, 149 (abstract).
Baba et al., "Catalytic methoxycarbonylation of aromatic diamines with dimethyl carbonate to their dicarbamates using zinc acetate," Catalysis Letteers, 2002, 82: 193-197 (abstract).
Baba et al., "Characteristics of methoxycarbonylation of aromatic diamine with dimethyl carbonate to dicarbamate using zinc acetate as catalyst," Green Chemistry, 2005, 7: 159-165 (abstract).
Reixach et al., "Zinc Acetates as Efficient Catalysts for the Synthesis of Bisisocyanate Precursors," Industrial and Engineering Chemistry Research, 2010, 49: 6362-6366 (abstract).
Reixach et al., "Alkoxycarbonylation of Industrially Relevant Anilines Using Zn4O(O2CCH3)6 as Catalyst," Industrial and Engineering Chemistry Research, 2012, 51: 16165-16170 (abstract).
Grego et al., "Phosgene-free Carbamoylation of aniline via dimethyl carbonate," Pure and Applied Chemistry, 2012, 84: 695-705.
Zhao et al., "Synthesis of Methyl N-Phenyl Carbamate Catalyzed by Ionic Liquid-Promoted Zinc Acetate," Industrial and Engineering Chemistry Research, 2012,51: 11335-11340 (abstract).
Wojciech et al., "Oxozinc Carboxylate Complexes: A New Synthetic Approach and the Carboxylate Ligand Effect on the Noncovalent-Interactions-Driven Self-Assembly," Inorganic Chemistry, 2012, 51: 7410-7414 (abstract).
McCowan et al., "Evidence for unimolecular CO2 elimination in C—N bond metathesis reactions of basic carbamatozinc complexes Zn4O (02CAm)6(Am=N-diethylamino, N-piperidyl, N-pyrrolidy)," Dalton Transactions, 2005, 2: 238 (abstract).
Orchard et al., "Organometallic Route to Surface-Modified ZnO Nanoparticles Suitable for In Situ Nanocomposite Synthesis: Bound Carboxylate Stoichiometry Controls Particle Size or Surface Coverage," Chemistry of Materials, 2012, 24: 2443-2448 (abstract).

(Continued)

*Primary Examiner* — Sudhakar Katakam
*Assistant Examiner* — Kofi Adzamli
(74) *Attorney, Agent, or Firm* — Donald R. Palladino

(57) ABSTRACT

The present invention relates to metallic zinc cluster compounds which are suitable as catalysts in the reaction of amines with dialkyl carbonates to produce carbamates. The invention is also directed towards a method for the alkoxycarbonylation of amines. The cluster compound has a general formula which may be written as $[M(O_2C-R)_2]_x \cdot [MO]_y \cdot [H_2O]_z$, wherein M is Zn, R is an unsubstituted or substituted aromatic, cycloaliphatic, linear aliphatic, or other organic rest, x is 1, y is ≥x is 1, y is ≥0.03 to ≤26.0 and z is >0.00 to ≤17.0.

15 Claims, 7 Drawing Sheets

(56) References Cited

OTHER PUBLICATIONS

Poshkus, Algirdas, "Improved Synthesis of Basic Zinc Acetate, Hexakis(u-acetato)-u-oxatetrazinc"; Ind. Eng. Chem. Prod. Res. Dev.; 1983; 22; pp. 380-381.
Dai et al., Synthesis and characterization of a novel precursor for thin films of zinc oxide by SSCVD, Science Direct, Materials Letters 61 (2007) 3539-3541.
Bury et al., Oxozinc carboxylates: a predesigned platform for modelling prototypical Zn-MOFs' reactivity toward water and donor solvents, ChemComm, 2012, 48, 7362-7364.

* cited by examiner

ZINC CLUSTER COMPOUNDS AND THEIR USE AS CATALYSTS IN THE REACTION OF AMINES WITH DIALKYL CARBONATES

CROSS-REFERENCE TO RELATED APPLICATIONS

This application is a National Phase Application of PCT/EP2014/060174, filed May 19, 2014, which claims priority to European Application No.: 13168788.1, filed May 22, 2013, each of which being incorporated herein by reference.

FIELD

The present invention relates to metallic zinc cluster compounds which are suitable as catalysts in the reaction of amines with dialkyl carbonates to produce carbamates. The invention is also directed towards a method for the alkoxycarbonylation of amines.

BACKGROUND

Carbamates are valuable intermediates in the production of agrochemicals, dyes, pharmaceutical compounds and, in particular, aromatic isocyanates used in the synthesis of polyurethanes. Most relevant from a commercial point of view are carbamates derived from 4,4'-methylenediphenylamine (MDA), its isomers and/or homologues or mixtures of the aforementioned compounds as obtained by acid catalyzed condensation/rearrangement reaction of aniline and formaldehyde, as well as 2,4-toluenediamine (TDA) or technical mixtures of the two TDA isomers 2,4-TDA and 2,6-TDA (approximately 80/20 mixtures). The aforementioned aromatic amines are used in the preparation of methylene diphenyl diisocyanate (MDI) and toluene diisocyanate (TDI), which are the direct precursors of polyurethanes. At present these isocyanates are produced industrially by phosgenation of the corresponding amines, a process which employs a toxic reagent (phosgene) and leads to large amounts of hydrochloric acid as side-product.

In the prior art, processes are known for the production of carbamates based on the functionalization of aromatic amines Ar—$NH_2$ with organic carbonates $ROCO_2R$ in the presence of suitable catalysts, according to the following scheme:

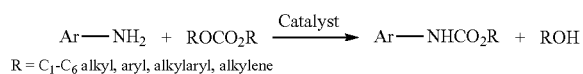

R = $C_1$-$C_6$ alkyl, aryl, alkylaryl, alkylene

In the case of aromatic diamines Ar(—$NH_2$)$_2$, biscarbamates are formed in a two-step reaction, with the corresponding monocarbamates being formed as intermediates, according to the following scheme:

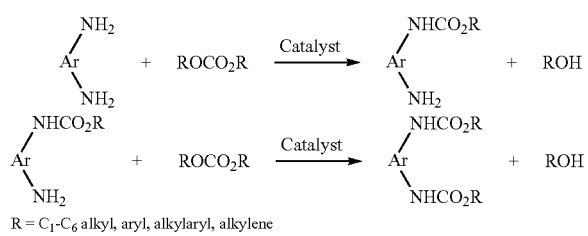

R = $C_1$-$C_6$ alkyl, aryl, alkylaryl, alkylene

Taking into account the alkylating properties of organic carbonates, N-alkylation competes with N-alkoxycarbonylation, and consequently N-alkylated products might be formed along the reaction, as well as products which are both N-alkylated and N-alkoxycarbonylated.

In the U.S. Pat. No. 3,763,217 it is disclosed that the Lewis acids $SbCl_5$, $SbCl_3$, $SbCl_2$, $AlCl_3$, $SbF_3$, $FeCl_3$, $UO_2(NO_3)_2$, $UO_2$, $UO_3$, $NbCl_5$ and $ThCl_4$ are suitable catalysts for reacting an organic carbonate with an aromatic amine to prepare carbamates. In the U.S. Pat. No. 4,268,683 and the European patent application EP-A-0065026 a process is disclosed for preparing carbamates from organic carbonates and aromatic amines in the presence of catalytic quantities of a Lewis acid catalyst. The catalyst should be soluble in the reaction mixture at the reaction conditions and be a member of the group consisting of a zinc or divalent tin halide, a zinc or divalent tin salt of a monovalent organic compound which has a pKa value of at least 2.8, and a zinc or divalent tin salt of trifluoroacetic acid. Among the zinc salts are mentioned: zinc chloride, zinc acetate, zinc acetate dihydrate, zinc oxyacetate ((AcOZn)$_2$O), zinc naphthenate, zinc octanoate, zinc propionate, zinc salicylate, zinc pivalate, zinc acrylate, zinc p-chlorobenzoate, zinc phenolate, zinc formate, zinc chloroacetate, zinc acetylacetonate, zinc oxalate, and zinc trifluoroacetate.

In the article of Baba et al., "Catalytic Synthesis of Dimethyl toluene-2,4-dicarbamate by the Methoxycarbonylation of 2,4-Toluenediamine with Dimethyl Carbonate Using Zn(OAc)$_2$.H$_2$O", *Science and Technology in Catalysis*, 2002, 149, the reaction of the amines MDA and TDA with dimethyl carbonate is described in the presence of a metal salt as catalyst to obtain the corresponding dicarbamates. Several salts of zinc, tin, lead and bismuth are mentioned. It is also disclosed that the selection of the metal salt is crucial for the formation of the carbamates. Among the catalysts some zinc carboxylates showed catalytic activity, while others were inactive. For instance, in the reaction of TDA with dimethyl carbonate, zinc acetate dihydrate as catalyst yielded 92% of dicarbamate, whereas zinc propionate yielded only 20% and zinc formate was completely inactive.

Another article of Baba et al., "Catalytic methoxycarbonylation of aromatic diamines with dimethyl carbonate to their dicarbamates using zinc acetate", *Catalysis Letters*, 2002, 82, 193-197, discloses the preparation of dicarbamates by methoxycarbonylation of TDA and MDA with dimethyl carbonate using zinc acetate dihydrate, or anhydrous zinc acetate as catalysts. The yield in the methoxycarbonylation of TDA with dimethyl carbonate using the hydrated catalyst is 92%, and using the anhydrous catalyst it is 98%. In the case of MDA the yield with zinc acetate dihydrate as catalyst is 98%.

Finally, in the article "Characteristics of methoxycarbonylation of aromatic diamine with dimethyl carbonate to dicarbamate using zinc acetate as catalyst", *Green Chemistry*, 2005, 7, 159-165, Baba et al. describe the reaction of the aromatic amines TDA and m-phenylenediamine with dimethyl carbonate in the presence of zinc acetate dihydrate as catalyst.

In the article "Zinc Acetates as Efficient Catalysts for the Synthesis of Bis-isocyanate Precursors", *Industrial and Engineering Chemistry Research*, 2010, 49, 6362-6366, Reixach et al. describe the use of zinc acetate dihydrate and anhydrous zinc acetate in alkoxycarbonylation of TDA and MDA using dimethylcarbonate and diethylcarbonate.

EP-A-1268409 describes the usage of zinc acetate dihydrate as catalyst in a continuous process for the manufacturing of aromatic carbamates by reaction of 80/20 mixtures of the two TDA isomers 2,4-TDA and 2,6-TDA with dimethyl carbonate. In EP-A-1255728, Zn salts such as zinc acetate or zinc acetate dihydrate (amongst other compounds) are mentioned as catalysts for the synthesis of aromatic carbamates by reaction of aromatic amines like 80/20 mixtures of the two TDA isomers 2,4-TDA and 2,6-TDA with dimethyl carbonate. Compounds or salts of Sn, Zn or Pb in particular are described as catalysts for the reaction of 2,4-TDA or technical mixtures of the two TDA isomers 2,4-TDA and 2,6-TDA with diethyl carbonate in EP-A-520273, or for the reaction of MDA (that is 4,4'-MDA, its isomers and/or homologues or mixtures of the aforementioned compounds as obtained by acid catalyzed condensation/rearrangement reaction of aniline and formaldehyde) with dialkyl carbonates like dimethyl carbonate or diethyl carbonate in EP-A-510459. In the European patent application EP-A-1958940, the inventors disclose processes for preparing azolynes, cyanoazolynes, symmetrical and unsymmetrical bisazolynes, amides, bisamides, cyanoamides, and peptides, which comprise the use of a metal catalyst defined by the general formula $Zn_a(OCOR7)_bZ2_c$, wherein R7 represents an optionally substituted alkyl group or an optionally substituted aryl group; Z2 represents an oxygen atom, a sulfur atom, or a selenium atom, "a" represents 1 or 4, "b" represents 2 or 6, and "c" represents 0 or 1; and provided that when "a" is 1, "b" is 2 and "c" is 0, and when "a" is 4, "b" is 6 and "c" is 1. The following zinc salts are specified in that patent application: zinc acetate, zinc trifluoroacetate, zinc acetoacetonate, zinc acetylacetonate, zinc trifluomethanesulfonate, and zinc p-toluenesulfonate. Furthermore, it is disclosed that certain tetranuclear zinc clusters may be used as catalysts, for instance: $Zn_4(OAc)_6O$, $Zn_4(OCOEt)_6O$, $Zn_4(OPv)_6O$, $Zn_4[OCO(CH_2)_{16}CH_3]_6O$, $Zn_4(OCOPh)_6O$ and $Zn_4(OCOCF_3)_6O$, wherein Ac represents an acetyl group, Et represents an ethyl group, Pv represents a pivaloyl group, and Ph represents a phenyl group. The zinc cluster $Zn_4(OAc)_6O$ is used in the preparation of oxazolynes and peptides.

EP 2 230 228 A1 and WO 2010/105768 A1 disclose a process for preparing aromatic carbamates using the tetranuclear zinc cluster $Zn_4(OAc)_6O$ as catalyst. In the article "Alkoxycarbonylation of Industrially Relevant Anilines Using $Zn_4O(O_2CCH_3)_6$ as Catalyst", *Industrial and Engineering Chemistry Research*, 2012, 51, 16165-16170, Reixach et al. describe the use of $Zn_4(OAc)_6O$ as catalyst for methoxy- and ethoxycarbonylation of a wide variety of amines, including 13 examples of aromatic amines.

Other contributions in this technical field include the reaction of aniline with dimethyl carbonate in the presence of homogeneous, heterogeneous and heterogenized (silica- or alumina-supported) zinc catalysts (Grego et al., *Pure and Applied Chemistry*, 2012, 84, 695-705). Furthermore, ionic liquid-promoted zinc acetate catalysts (Zn(OAc)2-ILs) have been reported to mediate the same reaction (Zhao et al., *Industrial and Engineering Chemistry Research*, 2012, 51, 11335-11340).

DETAILED DESCRIPTION

Figure 1:
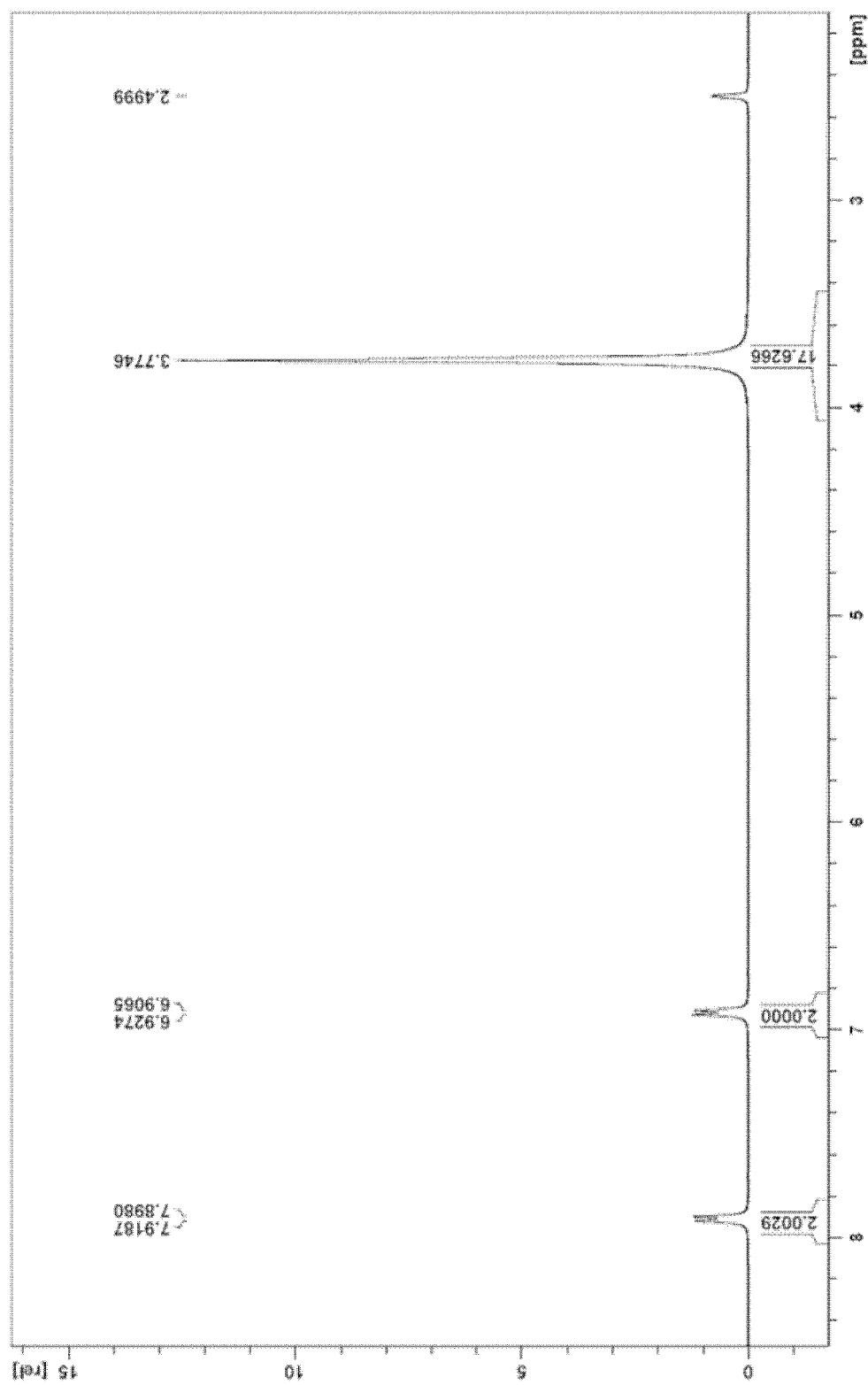
FIGS. 1-5 are analytical spectra of the catalyst according to example 1.

Taking into account the economic importance of carbamates as isocyanate precursors, it is highly desirable to provide new robust and functionalizable catalysts for the preparation of carbamates in high yield and with low amounts of by-products. Thus, the objective of the present invention is to provide new metallic clusters based on zinc and carboxylic acids, which are efficient and selective catalysts in the reaction of amines with dialkyl carbonates to produce carbamates. The invention is also directed towards a method for the alkoxycarbonylation of amines. According to the present invention this objective has been achieved by a compound of the formula:

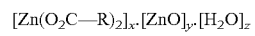

wherein R is an unsubstituted or substituted aromatic, cycloaliphatic, linear aliphatic, or other organic rest and x is 1, y is ≥0.03 to ≤26.0 and z is >0.00 to ≤17.0.

In contrast to the tetranuclear zinc clusters of the prior art discussed above, the compounds according to the invention contain OH groups. These are present in the form of crystal water (i.e. water that constitutes part of the molecular structure and cannot be removed without destruction) and/or bound to Zn (Zn—OH moiety).

The compounds according to the invention can be described as zinc clusters. Without wishing to be bound to a theory, the following structure is proposed (by way of example for R=p-$C_6H_4$—$CO_2^-$:

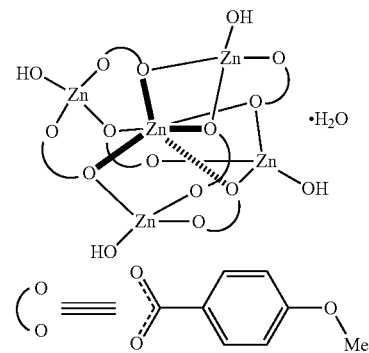

As will be shown in greater detail in the following description these zinc clusters efficiently mediate the methoxycarbonylation of amines, in particular MDA and TDA.

Suitable aryl groups which do not contain heteroatoms include, for example, phenyl and 1- and 2-naphthyl.

Suitable hetaryl groups include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, R can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5oxazolyl, 3-, 4- or 5-isoxazolyl, 2-, 4- or 5-thiazolyl, 3-, 4- or 5-isothiazolyl, 2-, 3 or 4-pyridyl, 2-, 4-, 5- or 6-pyrimidinyl, 1,2,3-triazol-1-,-4- or -5-yl, 1,2,4-triazol1-,-3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 62H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-6- or 7-benzisoxazolyl, 1-, 3-, 4-, 5-, 6- or 7benzothiazolyl, 2-, 4-, 5-, 6- or 7-benzisothiazolyl, 2-, 4-, 5-, 6- or 7-ben-1,3oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methyl-phenyl, 5-methyl-2-thienyl, 4-methyl-2thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

The term "cycloaliphatic", as used herein, refers to cyclic structures with or without alkyl substituents such that, for example, "C4 cycloaliphatic" includes methyl substituted cyclopropyl groups as well as cyclobutyl groups. The term "cycloaliphatic", as used herein also includes saturated heterocyclic groups.

Suitable halogen groups for substitution include F, Cl, Br, and/or I, from one to persubstitution (i.e. all H atoms on a group replaced by a halogen atom) being possible where an alkyl group is substituted by halogen, mixed substitution of halogen atom types also being possible on a given moiety.

The parameter y in the formula $[Zn(O_2C-R)2]_x \cdot [ZnO]_y \cdot [H_2O]_z$ is preferably $\geq 0.03$ to $<3.0$, more preferred $\geq 0.25$ to $\leq 2.0$ and most preferred $\geq 0.5$ to $\leq 1.0$. The parameter z in the formula is preferably $\geq 0$ to $\leq 3.0$, more preferred $\geq 0.25$ to $\leq 1.50$ and most preferred $\geq 0.50$ to $\leq 1.0$.

The present invention will be described with reference to further embodiments and aspects. They may be combined freely unless the context clearly indicates otherwise.

In one embodiment of the compound according to the invention R is selected from the group of $C_6H_5$, o-, m- and p-$C_6H_4$—OMe, o-, m- and p-$C_6H_4$—OH, p-$C_6H_4$—$NH_2$, p-$C_6H_4$—$NO_2$, p-$C_6H_4$—Br, o- and p-$C_6H_4$—$CO_2^-$, 2-pyrrolidinyl, heptadecanyl and/or $CH_2CH(OH)CO_2^-$.

In another embodiment of the compound according to the invention R is para-$C_6H_4$—$OCH_3$ and the zinc content as determined by thermogravimetric analysis is $\geq 20.0\%$ to $\leq 45.0\%$, preferably $\geq 23.0\%$ to $\leq 30.0\%$.

In another embodiment of the compound according to the invention R is para-$C_6H_4$—$OCH_3$ and the carbon content as determined by elemental analysis is $\geq 30.0\%$ to $\leq 48.0\%$, preferably $\geq 40.0\%$ to $\leq 45.0\%$.

The present invention is also directed towards a method for producing a compound according to the invention, comprising the steps of:
A) providing an aqueous solution comprising a carboxylic acid $HO_2C$—R and a base, wherein R is an unsubstituted or substituted aromatic, cycloaliphatic, linear aliphatic, or other organic rest;
B) providing an aqueous solution comprising a dissolved zinc salt;
C) combining the solutions of step A) and step B) and optionally adding extra water.

Regarding the rest R in the carboxylic acid in A), the same comments as already outlined above in connection with the compound according to the invention apply. For reasons of brevity they are not repeated here.

The base used in step A) should of course be sufficiently strong to at least partially deprotonate the carboxylic acid $HO_2C$—R.

After combining the solutions of A) and B) the precipitated desired zinc compound can be recovered, washed and dried.

For solution A) the concentration of the carboxylic acid $HO_2C$—R is preferably $\geq 0.25$ M to $\leq 0.60$ M and the concentration of the base is preferably $\geq 0.39$ M to $\leq 0.76$ M. For solution B) the concentration of zinc ions is preferably $\geq 0.13$ M to $\leq 0.51$ M. After combining the solutions A) and B) and optionally adding extra water, the concentration of zinc is preferably $\geq 0.04$ M to $\leq 0.26$ M.

An example for typical concentrations is: solution A) 0.5 M of carboxylic acid and 0.75 M of base, and for solution B) 0.31 M of Zn. After combination of A) and B) [Zn] is 0.14 M without adding extra water and 0.09 M after addition of extra water.

In one embodiment of the method according to the invention R is selected from the group of $C_6H_5$, o-, m- and p-$C_6H_4$—OMe, o-, m- and p-$C_6H_4$—OH, p-$C_6H_4$—$NH_2$, p-$C_6H_4$—$NO_2$, p-$C_6H_4$—Br, o- and p-$C_6H_4$—$CO_2^-$, 2-pyrrolidinyl, heptadecanyl and/or $CH_2CH(OH)CO_2^-$.

In another embodiment of the method according to the invention the zinc salt is zinc sulfate and/or zinc sulfate heptahydrate.

In another embodiment of the method according to the invention the base in step A) is sodium hydrogen carbonate and/or sodium hydroxide.

In another embodiment of the method according to the invention, during step C) the solution of step A) is added to the solution of step B). This can be undertaken in a batch-wise, drop-wise or continuous fashion.

In another embodiment of the method according to the invention, during step C) the solution of step A) has a temperature of $\geq 30°$ C. to $\leq 90°$ C., preferably $\geq 40°$ C. to $\leq 60°$ C.

In another embodiment of the method according to the invention, during step C) the solution of step B) has a temperature of $\geq 18°$ C. to $\leq 30°$ C., preferably $\geq 20°$ C. to $\leq 25°$ C.

In another embodiment of the method according to the invention, after step C) it is waited for a time period of $\geq 30$ minutes to $\leq 1500$ minutes before the product is isolated, preferably $\geq 60$ minutes to $\leq 180$ minutes.

A further aspect of the invention is a method of producing carbamate compounds, comprising the step of reacting an organic amine with a dialkyl carbonate in the presence of a catalyst, wherein the catalyst comprises a compound of the formula

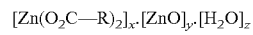

wherein R is an unsubstituted or substituted aromatic, cycloaliphatic, linear aliphatic, or other organic rest and x is 1, y is $\geq 0.03$ to $\leq 26.0$ and z is $>0.00$ to $\leq 17.0$.

The parameter y in the formula $[Zn(O_2C-R)_2]_x \cdot [ZnO]_y \cdot [H_2O]_z$ is preferably $\geq 0.03$ to $<3.0$, more preferred $\geq 0.25$ to $\leq 2.0$ and most preferred $\geq 0.5$ to $\leq 1.0$. The parameter z in the formula is preferably $>0$ to $<3.0$, more preferred $\geq 0.25$ to $\leq 1.50$ and most preferred $\geq 0.50$ to $\leq 1.0$.

Regarding the rest R, the same comments as already outlined above in connection with the compound according to the invention apply. For reasons of brevity they are not repeated here. The same holds for the parameters y and z including their preferred ranges.

In particular, a zinc compound according to the invention may be used as a catalyst.

The method according to this invention may for example use aliphatic, cycloaliphatic or aromatic amines or a mixture of two or more amine compounds as a starting material. The aromatic amine is a compound having at least one aromatic ring and at least one amino group bound to the aromatic ring. When the aromatic amine has more than one aromatic ring, the rings may be condensed or joined by at least one common ring member, a bond between a ring member of each aromatic ring or a divalent moiety. The divalent moiety preferably comprises C, O, S or N, more preferably from 1 to 6 C atoms. In a preferred embodiment, the divalent moiety is methylene.

At least one substituent of an aromatic amine is an amino group. Preferably at least two substituents, preferably up to four substituents, and even more preferably two substituents, are amino groups. The amino groups are preferably primary or secondary amino groups, and more preferably primary amino groups. Preferably, at least one amino group is in the 2-, 4- or 6-position, more preferably at least one amino group is in the 2-position, relative to a hydrocarbon group, preferably a methyl group, substituent on at least one, preferably only one, aromatic ring. More preferably, amino groups are present in the 2- and the 4- or 6-position of at least one, preferably only one, aromatic ring. In general, examples for aromatic amines include:

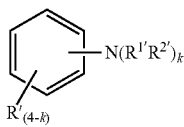

wherein R' is hydrogen, halogen, linear or branched C1-C12 alkyl, linear or branched C1-C12 alkoxy, linear or branched C1-C12 alkoxyalkyl, or C1-C12 alkylamino; $R^{1'}$ and $R^{2'}$ are independently hydrogen, or linear or branched C1-C12 alkyl; k is an integer 2-4.

Other examples include:

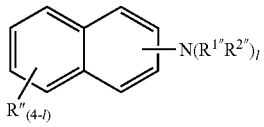

wherein R" is hydrogen, halogen, linear or branched C1-C12 alkyl, linear or branched C1-C12 alkoxy, linear or branched C1-C12 alkoxyalkyl, or C1-C12 alkylamino; $R^{1''}$ and $R^{2''}$ are independently hydrogen, or linear or branched C1-C12 alkyl; l is an integer 2-4; and the substituents R" and $NR^{1''}R^{2''}$ can be present at any position of the naphthalene ring.

Further examples include:

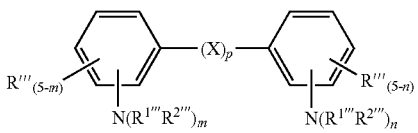

wherein R''' is hydrogen, halogen, linear or branched C1-C12 alkyl, linear or branched C1-C12 alkoxy, linear or branched C1-C12 alkoxyalkyl, or C1-C12 alkylamino; $R^{1'''}$ and $R^{2'''}$ are independently hydrogen, or linear or branched C1-C12 alkyl; X is linear or branched C1-C6 alkylene, O, S, NR'''; m and n is 0 or an integer 1-3 and m+n≥2; and p is 0 or 1.

In one embodiment of this method in the catalyst compound R is selected from the group of $C_6H_5$, o-, m- and p-$C_6H_4$—OMe, o-, m- and p-$C_6H_4$—OH, p-$C_6H_4$—$NH_2$, p-$C_6H_4$—$NO_2$, p-$C_6H_4$—Br, o- and p-$C_6H_4$—$CO_2^-$, 2-pyrrolidinyl, heptadecanyl and/or $CH_2CH(OH)CO_2^-$.

In another embodiment of this method the organic amine is an aromatic amine selected from the group of 2,4-diamino-n-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o, m, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'oxydianiline, 4,4'ethylenedianiline, 2,4-bis(4-aminobenzyl)aniline, 4,4'methylenebis(N,N-dimethylaniline); 4,4'methylenebis(N-methylaniline); benzidine; N,N,N',N'-tetramethylbenzidine, bis(3,4-diaminophenyl)methane, bis(3-methyl-4-aminophenyl)methane, 2,2',2,4' or 4,4'-methylene dianiline, 1,6-hexamethylene diamine, isophorone diamine, (2-aminocyclohexyl)-(4'-aminocyclohexyl)-methane and/or bis-(4-aminocyclohexyl)-methane.

In another embodiment of this method the amine is a mixture of 2,4-toluylene diamine and 2,6-toluylene diamine. Preferably this is a technical mixture such as 80% 2,4-TDA and 20% 2,6-TDA.

The present invention will now be described with reference to the following examples without wishing to be limited thereto.

EXAMPLES

Example 1: Catalyst Preparation

Batch 1:

A mixture of 4-methoxybenzoic acid (7.66 g, 99%, 49.8 mmol) and sodium hydrogen carbonate (6.45 g, 76.8 mmol) in distilled water (100 mL) was heated until all the solid had dissolved. A solution of zinc sulfate heptahydrate (7.27 g, 99%, 25.0 mmol) in distilled water (80 mL) was prepared. The first solution was added to the second while the first one was at 50° C. and the second one at RT. A white compound precipitated immediately forming a dense suspension. Distilled water (RT, 100 mL) was added and the mixture was allowed to stand for 1.5 h, during which it was gently shaken from time to time. The reaction was worked up when the precipitate settled on the bottom of the reaction flask.

The reaction mixture was then filtered over a glass frit. The residue was washed with water (3×25 mL) and EtOH (1×25 mL) and dried on the filter. Finally it was washed with DCM (2×25 mL) and dried overnight in a vacuum oven at 120° C. and 1 mbar. A finely dispersed white powder is obtained. The zinc content of this material was estimated at 25.6% using thermogravimetric analysis (TGA; air, 30-1000° C.). Yield: 5.5 g, 86%.

$^1$H NMR (DMSO-$d_6$) δ 7.91 (d, J=8.3 Hz, 12H, ArH), 6.92 (d, J=8.4 Hz, 12H, ArH), 3.77 (s, 18H, —OCH$_3$); $^{13}$C NMR (DMSO-$d_6$) δ 172.5 (q), 162.1 (q), 131.9 (t), 127.1 (q), 113.5 (t), 55.6 (p); FT-IR (neat, cm$^{-1}$): 3554, 2938, 2837, 1605, 1590, 1547, 1511, 1458, 1389, 1313, 1298, 1249, 1171, 1145, 1103, 1024, 848, 779, 699, 642, 623, 563, 502, 455; thermogravimetric analysis (TGA; N$_2$, 30-500° C., 10° C./min): mass loss between 40 and 230° C. (3.01%) and >320° C.; differential scanning calorimetry (DSC; N$_2$, 30-500° C., 10° C./min): phase transitions at 190° C. (endothermic, accompanied by mass loss) and 306° C. (endothermic, m.p.); purity calculation based on DSC (based on peak at 306° C.): 99.3%; zinc content (TGA, air, 30-1000° C., 10° C./min, residue is assumed to consist entirely of Zn O): 25.6%; Anal. calcd. for [Zn(O$_2$C—C$_6$H$_4$-p-OCH$_3$)$_2$]$_1$ [ZnO]$_{0.65}$[H$_2$O]$_{0.62}$: C, 44.51; H, 3.56; Zn, 24.99. found: C, 44.53; H, 3.56.

Repetitions of the reaction described above yielded products with the same spectroscopic data and the following elemental analyses:

Batch 2:
Anal. calcd. for $[Zn(O_2C-C_6H_4-p-OCH_3)_2]_1 \cdot [ZnO]_{0.59} \cdot [H_2O]_{0.99}$: C, 44.33; H, 3.72; Zn, 24.08. found: C, 44.29; H, 3.72. Zinc content (TGA): 25.4%.

Batch 3:
Anal. calcd. for $[Zn(O_2C-C_6H_4-p-OCH_3)_2]_1 \cdot [ZnO]_{0.60} \cdot [H_2O]_{0.86}$: C, 44.39; H, 3.67; Zn, 24.22. found: C, 44.52; H, 3.67. Zinc content (TGA): 24.9%.

Batch 4:
Anal. calcd. for $[Zn(O_2C-C_6H_4-p-OCH_3)_2]_1 \cdot [ZnO]_{0.97} \cdot [H_2O]_{0.50}$: C, 42.18; H, 3.32; Zn, 28.27. found: C, 42.21; H, 3.32. Zinc content (TGA): 28.6%.

Figure 2:
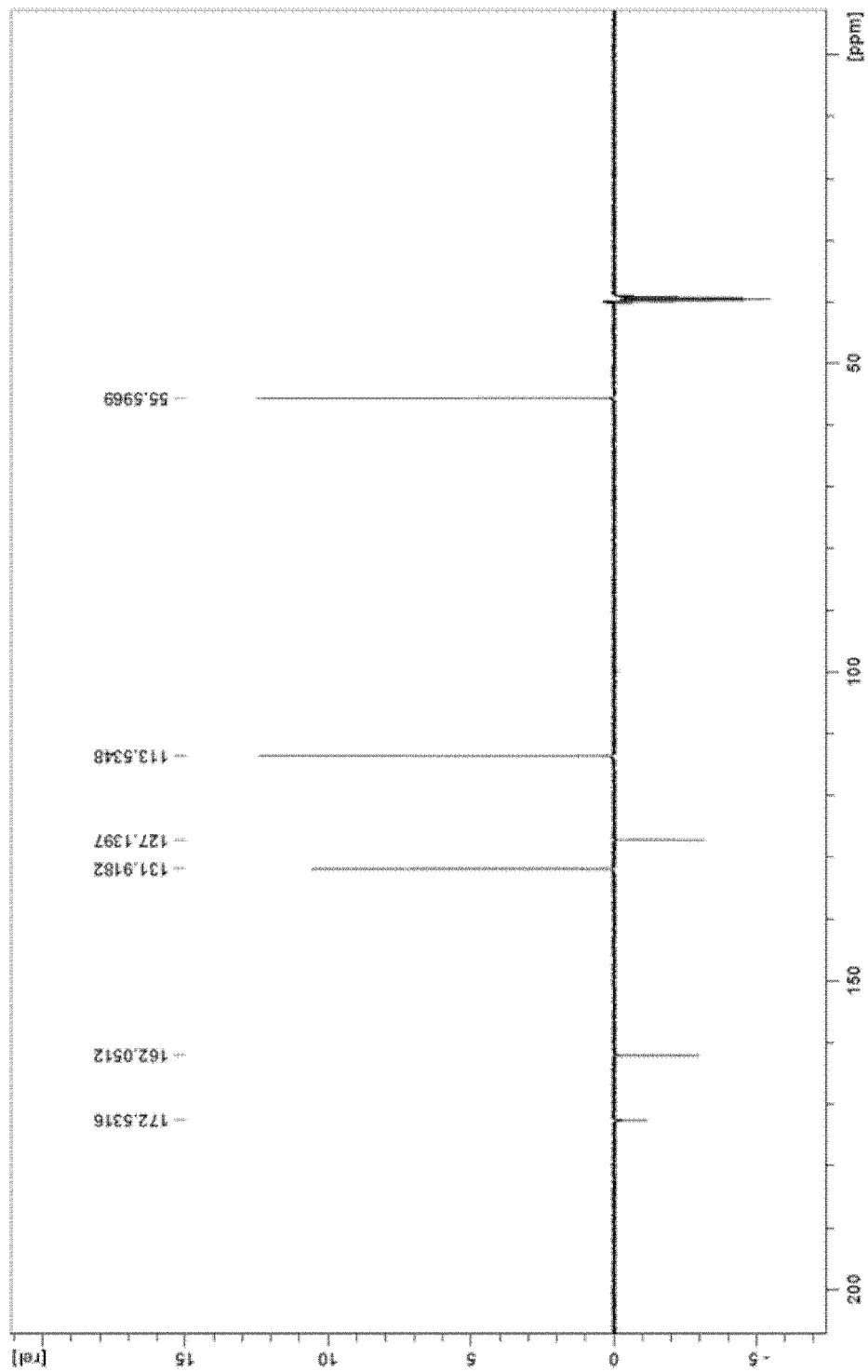
Figure 3:
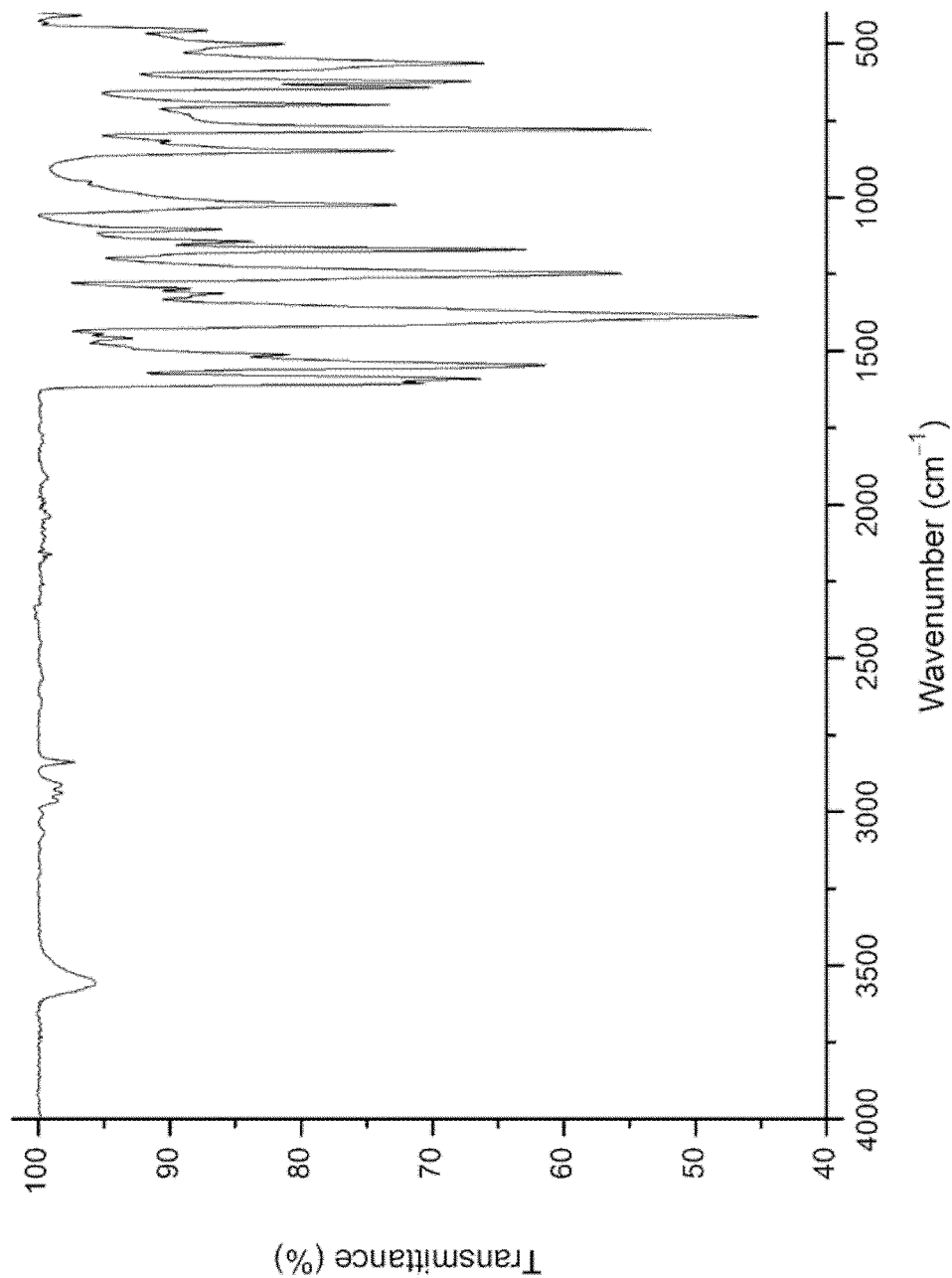
Figure 4:
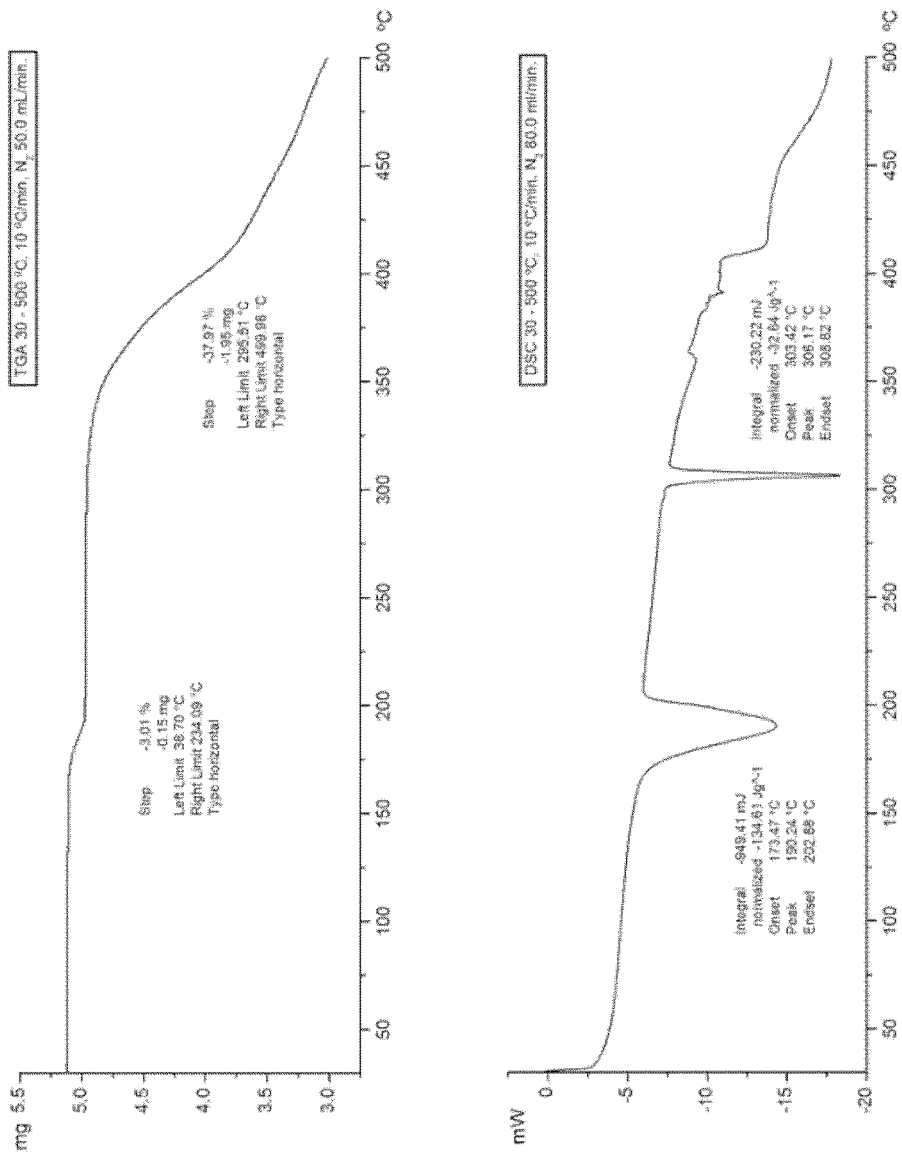
Figure 5:
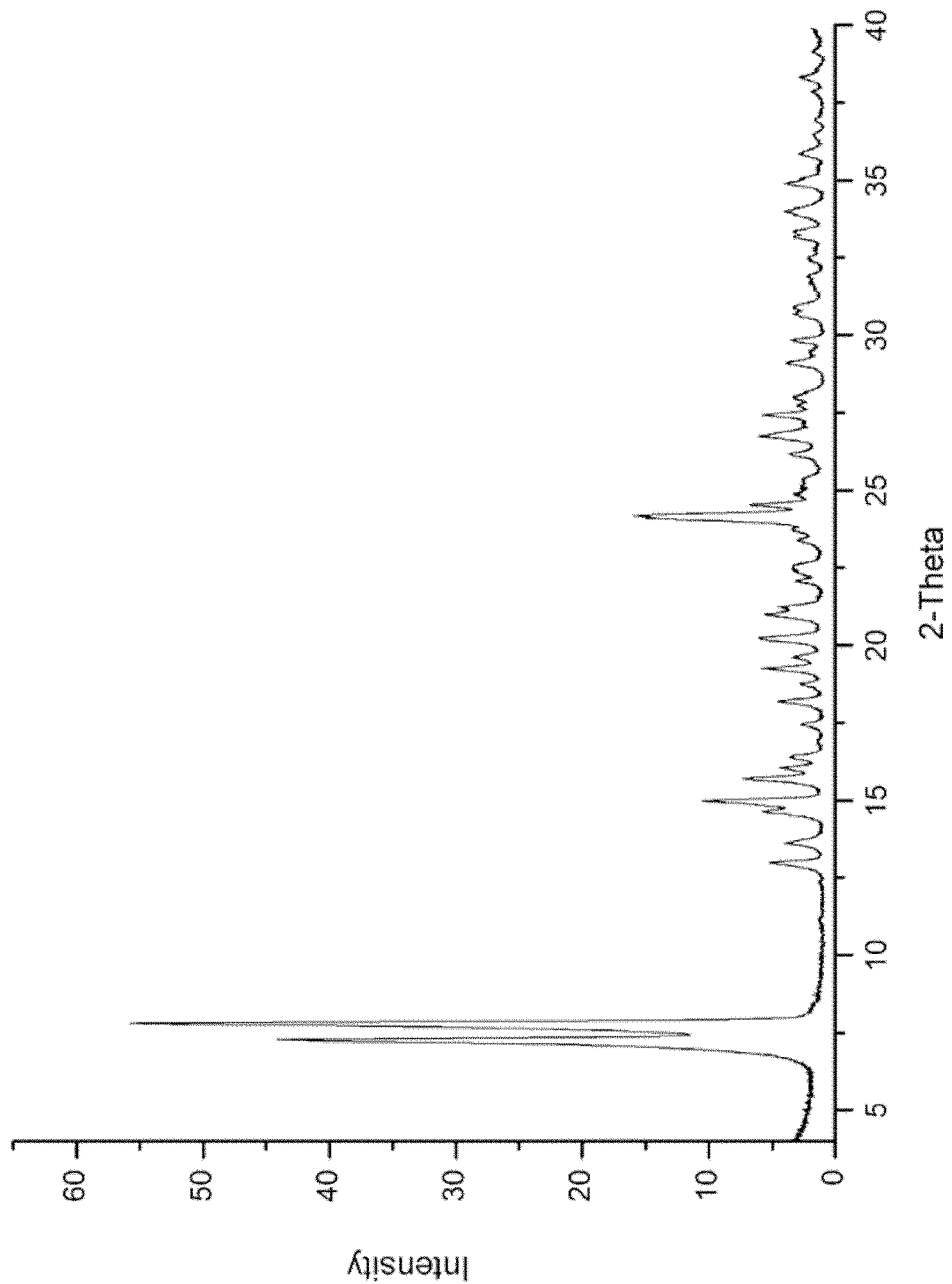

Analytical spectra of the catalyst according to example 1 are shown in FIGS. 1 to 5. The $^1$H NMR, $^{13}$C (APT) NMR and IR spectra, which are shown in FIGS. 1, 2 and 3, respectively, appear to indicate that the obtained product is zinc para-methoxybenzoate. However, thermal analysis (TGA and DSC, FIG. 4) shows loss of mass around 190° C. [TGA of zinc para-methoxybenzoate does not show loss of mass at this temperature], as well as a different melting point [306° C. instead of 278° C. for zinc para-methoxybenzoate]. Also the XRPD spectrum (FIG. 5) is different than that of zinc para-methoxybenzoate. Together, these data confirm the results of elemental analysis, that a material different from zinc para-methoxybenzoate has been obtained.

Example 2: Methoxycarbonylation of Aromatic Amines with Dimethyl Carbonate (DMC)

The catalytic results presented below are based on a series of reactions using four different batches of the catalyst and a minimum of two reactions per catalyst batch. Each reaction was analyzed in duplo or triplo.

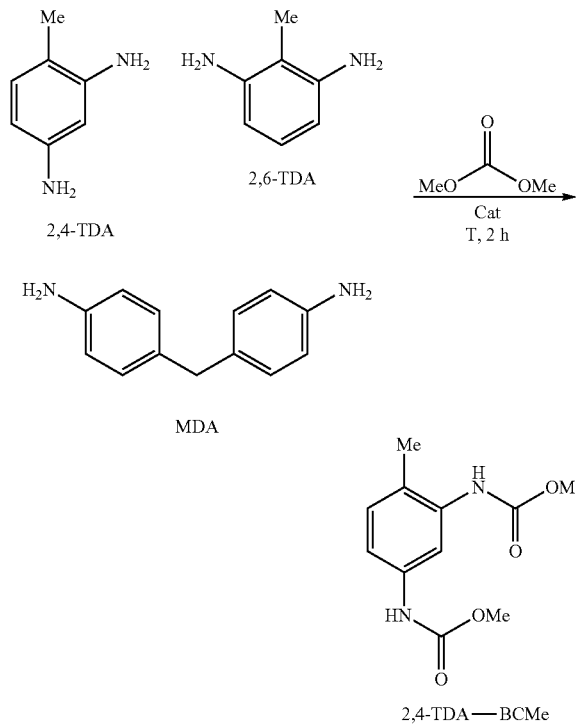

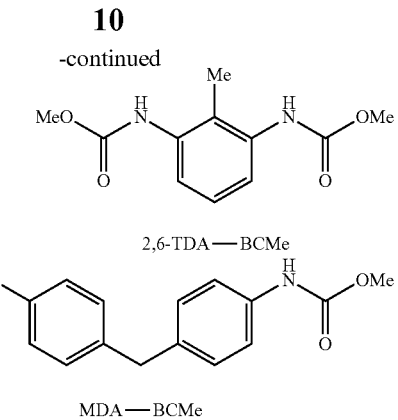

For reactions with TDA: 30 molar equivalents of DMC, 2.5 mol % Zn, T=190° C.

For reactions with MDA: 25 molar equivalents of DMC, 1.0 mol % Zn, T=180° C.

Reactions are performed in an autoclave. The reaction time of 2 h refers to the time the reaction is allowed to proceed after the desired temperature has been reached. Heating up the autoclave takes 50 min for reactions at 180° C. or 60 min for reactions at 190° C.

The results are summarized in the following table:

| Substrate | Average Yield biscarbamate (%) | Number of reactions |
| --- | --- | --- |
| 2,4-TDA | 96 ± 1 | 12 |
| 2,6-TDA | 69 ± 5 | 10 |
| 2,4-/2,6-TDA 80:20 | 98 ± 1/87 ± 2 | 11 |
| MDA | 96 ± 1 | 8 |

The methoxycarbonylation of 2,6-TDA was found to give slightly lower yields and the reaction results displayed a larger standard deviation. Interestingly, when a 80:20 mixture of 2,4- and 2,6-TDA is used, both of the substrates behave better than when used on their own.

Example 3: Comparative Examples

It should be recalled at this point that catalyst according to the invention ($[Zn(O_2C-C_6H_4-p-OCH_3)_2]_x \cdot [ZnO]_y \cdot [H_2O]_z$) presented a higher catalytic activity than observed for the isolated components when used as catalysts.

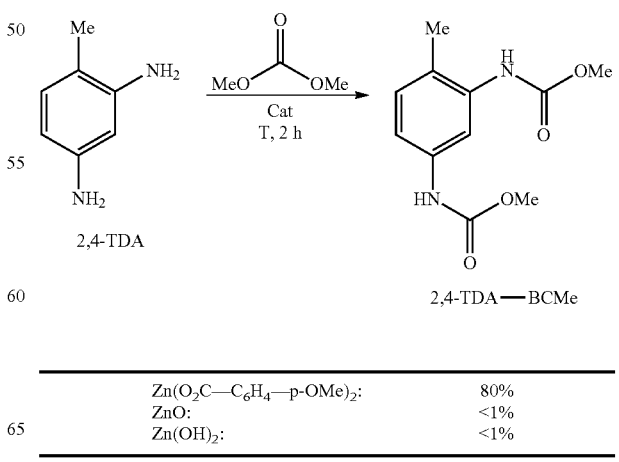

| | |
| --- | --- |
| $Zn(O_2C-C_6H_4-p-OMe)_2$: | 80% |
| ZnO: | <1% |
| $Zn(OH)_2$: | <1% |

It is worth noting that, as a general rule, analytically pure aromatic zinc carboxylates (no ZnO or Zn(OH)$_2$ moieties) give rather poor yields in the methoxycarbonylation of TDA:

| Catalyst | Yield of 2,4-TDA-BCMe (%) |
|---|---|
| Zn(O$_2$C—C$_6$H$_5$)$_2$ | 85 |
| Zn(O$_2$C—C$_6$H$_4$—p-OCH$_3$)$_2$ | 80 |
| Zn(O$_2$C—C$_6$H$_4$—p-NO$_2$)$_2$•2H$_2$O | 87 |

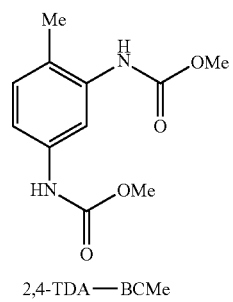

2,4-TDA—BCMe

| t (min) | 2,4-TDA (%) | 2,4-TDA-MC-p-Me (%) | 2,4-TDA-MC-o-Me (%) | 2,4-TDA-BCMe (%) | T (°C.) |
|---|---|---|---|---|---|
| 0 | 100 | 0 | 0 | 0 | 27 ± 1 |
| 15 | 99.2 ± 0.0 | 0.7 ± 0.1 | 0.1 ± 0.0 | 0.0 ± 0.0 | 94 ± 1 |
| 30 | 73.9 ± 6.0 | 21.9 ± 5.5 | 3.3 ± 0.8 | 0.9 ± 0.3 | 148 ± 1 |
| 40 | 23.6 ± 4.7 | 60.5 ± 2.9 | 6.7 ± 0.2 | 9.2 ± 1.4 | 164 ± 1 |
| 45 | 11.6 ± 5.0 | 65.5 ± 1.5 | 5.6 ± 0.7 | 17.3 ± 4.3 | 172 ± 3 |
| 50 | 1.3 ± 0.2 | 61.3 ± 1.3 | 2.3 ± 0.2 | 35.1 ± 1.8 | 181 ± 1 |
| 60 | 0.2 ± 0.1 | 40.0 ± 8.8 | 0.6 ± 0.2 | 57.6 ± 7.8 | 190 ± 1 |
| 90 | 0.1 ± 0.0 | 5.1 ± 1.5 | 0.2 ± 0.0 | 90.6 ± 1.9 | 190 ± 1 |
| 135 | 0.0 ± 0.0 | 1.2 ± 0.2 | 0.2 ± 0.0 | 96.5 ± 1.4 | 190 ± 1 |
| 180 | 0.0 ± 0.0 | 0.8 ± 0.1 | 0.1 ± 0.0 | 97.6 ± 1.4 | 190 ± 1 |
| 240 | 0.0 ± 0.0 | 0.8 ± 0.0 | 0.2 ± 0.0 | 96.0 ± 0.9 | 190 ± 1 |

Example 4: Kinetic Profiles

A kinetic profile of the methoxycarbonylation of 2,4-TDA was made based on a series of independent reactions that were stopped at t=15, 30, 40, 45, 50, 60, 90, 135, 180, and 240 min. Reactions were performed in duplo (t=15, 90, 135, 180 and 240 min), triplo (t:=30 and 40 min) or quadruplo (t=45, 50 and 60 min). The results are summarized in the table below. Percentages given are molar fractions of starting material and products, as determined by HPLC using external standards (calibration curves).

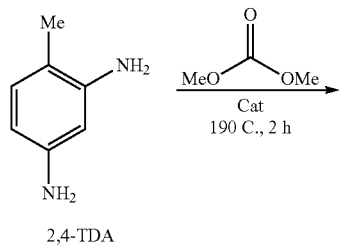

2,4-TDA

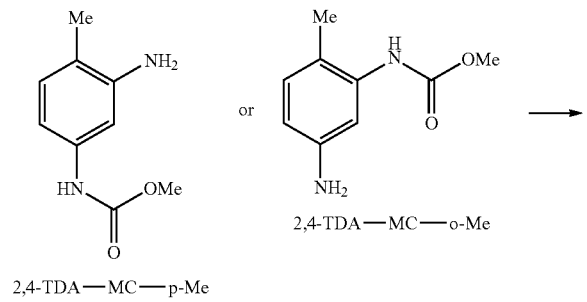

2,4-TDA—MC—p-Me          2,4-TDA—MC—o-Me

Figure 6:
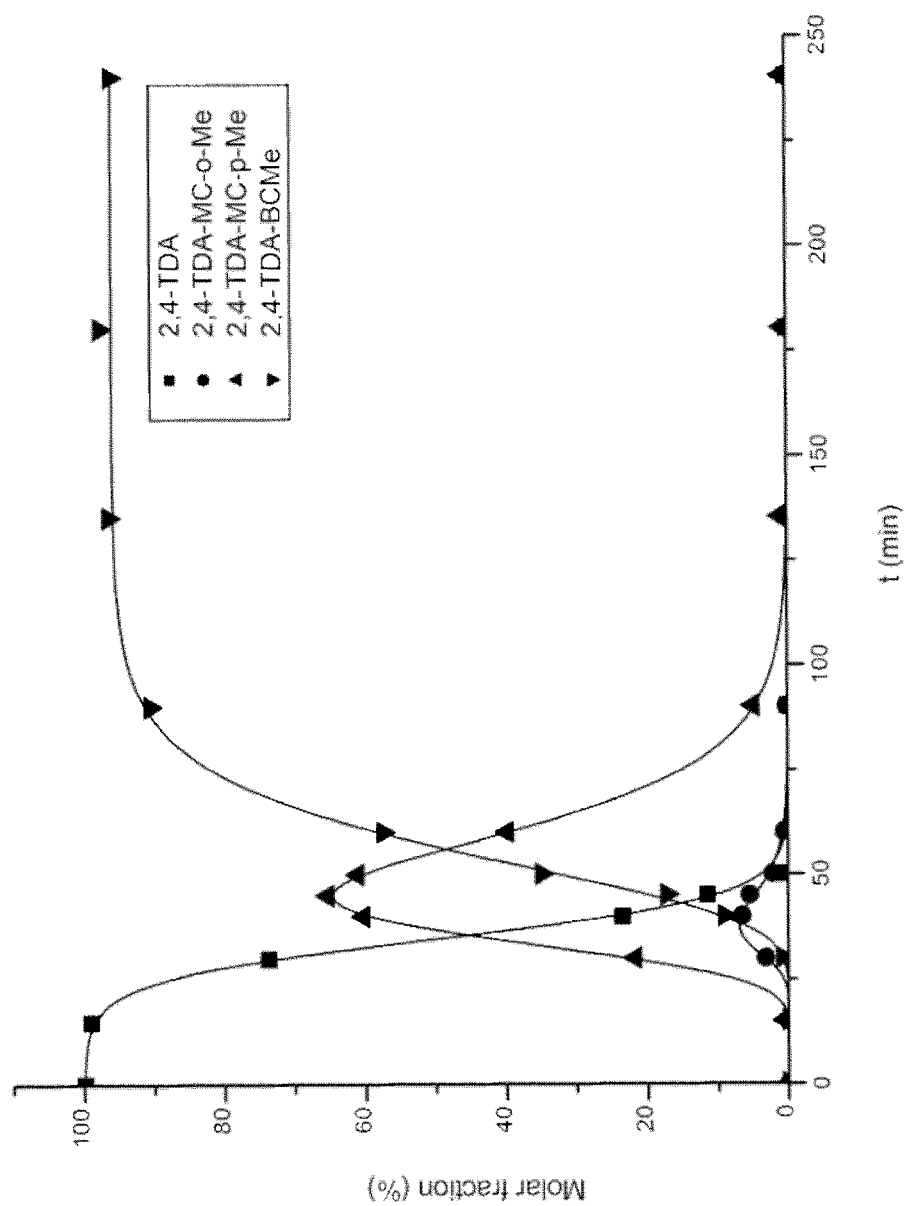
FIGS. 6 and 7 illustrate the results of reactions of example 4.

This is also shown in FIG. 6.

Figure 7:
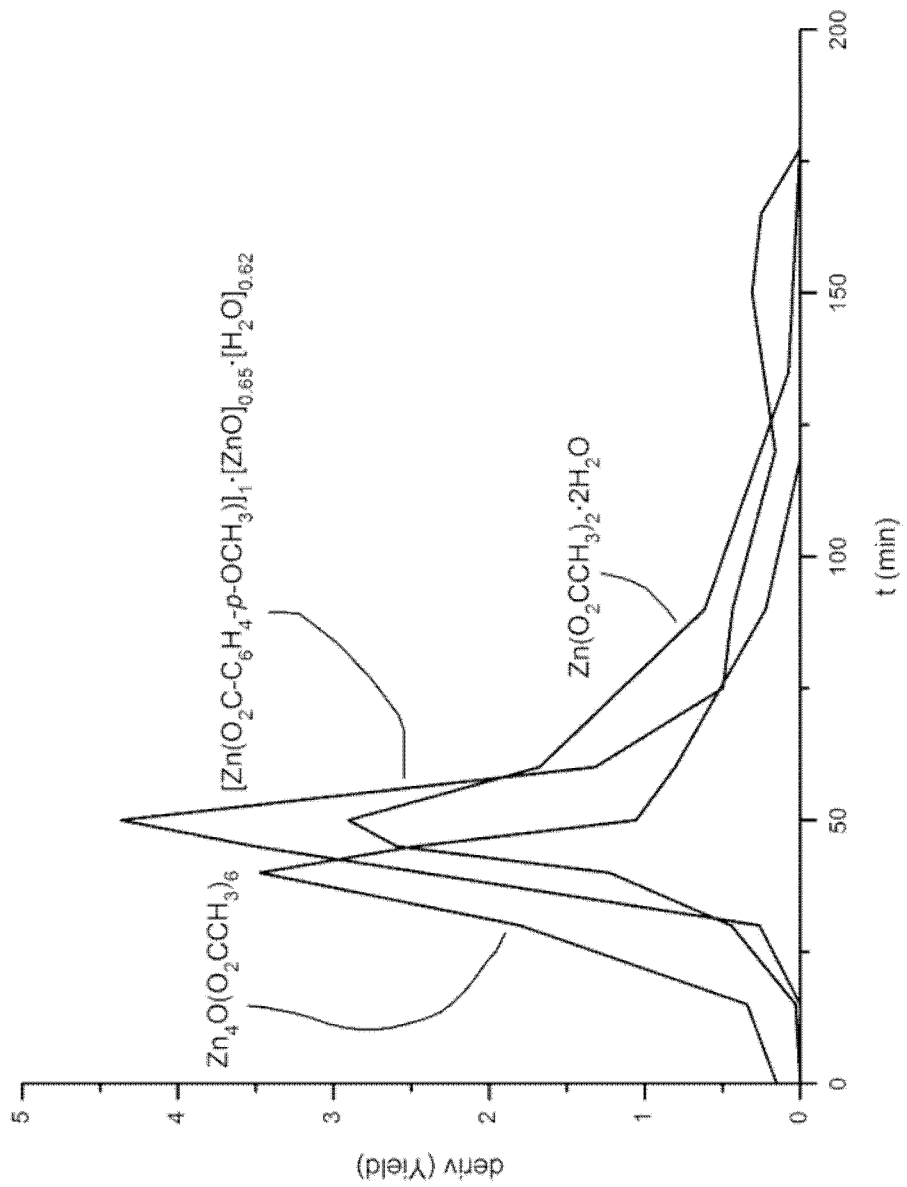

The maximum rate in the alkoxycarbonylation of 2,4-TDA mediated by the catalyst according to the invention is observed at 50 min. This catalyst shows a slightly higher maximum rate than the ones observed for Zn$_4$O(OAc)$_6$ and for zinc acetate dihydrate (cf. FIG. 7).

The invention claimed is:

1. A compound of the formula

[Zn(O$_2$C—R)$_2$]$_x$·[ZnO]$_y$·[H$_2$O]$_z$, wherein R is selected from the group of C$_6$H$_5$, o-, m- and p-C$_6$H$_4$—OMe, o-, m- and p-C$_6$H$_4$—OH, p-C$_6$H$_4$NH$_2$, p-C$_6$H$_4$—NO$_2$, p-C$_6$H$_4$—Br, o- and p-C$_6$H$_4$—CO$_2$—, 2-pyrrolidinyl, heptadecanyl and/or CH$_2$CH(OH)CO$_2$—;

x is 1, y is ≥0.03 to ≤3.0 and z is >0 to ≤3.0.

2. The compound of claim 1, wherein R is para-C$_6$H$_4$—OCH$_3$ and wherein the zinc content as determined by thermogravimetric analysis is ≥20.0% to ≤45.0%.

3. The compound of claim 1, wherein R is para-C$_6$H$_4$—OCH$_3$ and wherein the carbon content as determined by elemental analysis is ≥30.0% to ≤48.0%.

4. A method for producing the compound of claim 1, comprising the steps of:
   A) providing an aqueous solution comprising a carboxylic acid HO$_2$C—R and a base, wherein R is an unsubstituted or substituted aromatic, cycloaliphatic, or linear aliphatic organic rest;
   B) providing an aqueous solution comprising a dissolved zinc salt; and
   C) combining the solutions of step A) and step B).

5. The method of claim 4, wherein the zinc salt is zinc sulfate and/or zinc sulfate heptahydrate.

6. The method of claim 4, wherein the base in step A) is sodium hydrogen carbonate and/or sodium hydroxide.

7. The method of claim 4, wherein during step C) the solution of step A) is added to the solution of step B).

8. The method of claim 4, wherein during step C) the solution of step A) has a temperature of ≥30° C. to ≤90° C.

9. The method of claim 4, wherein during step C) the solution of step B) has a temperature of ≥18° C. to ≤30° C.

10. The method of claim 4, further comprising waiting after step C) for ≥30 minutes to ≤1500 minutes before isolating the compound.

11. A method of producing carbamate compounds, comprising the step of reacting an organic amine with a dialkyl carbonate in the presence of a catalyst comprising the compound of claim 1.

12. The method of claim 11, wherein the organic amine is an aromatic amine selected from the group of 2,4-diamino-n-phenylaniline, o-, m, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o, m, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'oxydianiline, 4,4'ethylenedianiline, 2,4-bis(4-aminobenzyl)aniline, 4,4'methylenebis(N,N-dimethylaniline); 4,4'methylenebis(N-methylaniline); benzidine; N,N,N',N'-tetramethylbenzidine, bis(3,4-diaminophenyl)methane, bis(3-methyl-4-aminophenyl)methane, 2,2', 2,4' or 4,4'-methylene dianiline, 1,6-hexamethylene diamine, isophorone diamine, (2-aminocyclohexyl)-(4'-aminocyclohexyl)-methane and/or bis-(4-aminocyclohexyl)-methane.

13. The compound of claim 1, wherein x is 1, y is ≥0.5 to ≤1.0, and z is ≥0.50 to ≤1.0.

14. The method of claim 11, wherein x is 1, y is ≥0.5 to ≤1.0, and z is ≥0.50 to ≤1.0.

15. The compound of claim 3, wherein R is para-$C_6H_4$—$OCH_3$ and wherein the carbon content as determined by elemental analysis is ≥40.0 and ≤45.0.

* * * * *